(12) United States Patent
Narita et al.

(10) Patent No.: US 7,597,863 B2
(45) Date of Patent: Oct. 6, 2009

(54) EXTRACTANT FOR PALLADIUM AND METHOD FOR SEPARATION AND RECOVERY OF PALLADIUM

(75) Inventors: Hirokazu Narita, Ibaraki (JP); Mikiya Tanaka, Ibaraki (JP)

(73) Assignee: National Institute of Advanced Industrial Science & Technology, Tokyo (JP)

( * ) Notice: Subject to any disclaimer, the term of this patent is extended or adjusted under 35 U.S.C. 154(b) by 380 days.

(21) Appl. No.: 10/590,799

(22) PCT Filed: Feb. 23, 2005

(86) PCT No.: PCT/JP2005/002855

§ 371 (c)(1),
(2), (4) Date: Aug. 25, 2006

(87) PCT Pub. No.: WO2005/083131

PCT Pub. Date: Sep. 9, 2005

(65) Prior Publication Data

US 2007/0172404 A1    Jul. 26, 2007

(30) Foreign Application Priority Data

Feb. 27, 2004   (JP)   ............................. 2004-055420

(51) Int. Cl.
*C22B 11/00* (2006.01)
(52) U.S. Cl. ...................................... 423/22
(58) Field of Classification Search ........................ None
See application file for complete search history.

(56) References Cited

U.S. PATENT DOCUMENTS 4,390,366 A * 6/1983 Lea et al. ...................... 75/423

(Continued)

FOREIGN PATENT DOCUMENTS

JP    63-14824    1/1988

(Continued)

OTHER PUBLICATIONS

Hagermann, Justin et al, Designer Ligands, Jan. 1, 1999, Synthetic Communications, 29:2, 303-310.*

(Continued)

*Primary Examiner*—Melvin C Mayes
*Assistant Examiner*—Stefanie Cohen
(74) *Attorney, Agent, or Firm*—Morgan, Lewis & Bockius LLP

(57) ABSTRACT

There is provided a novel extractant for palladium capable of improving an extraction speed in comparison with a case of utilizing a DHS being a conventional extractant, and a method for separation and recovery of palladium utilizing the same. The present invention provides a method for obtaining a palladium-containing aqueous solution by bringing an organic phase containing an extractant of a sulfur-containing diamide compound represented by the following structural formula (1):

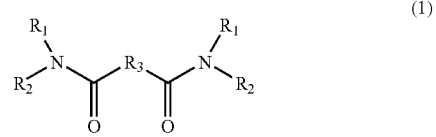

(1)

in which $R_1$ and $R_2$ each represent a group selected from a chain hydrocarbon group having 1 to 18 carbon atoms which may be branched, an alicyclic hydrocarbon group having 1 to 10 carbon atoms, and an aromatic hydrocarbon group having 1 to 14 carbon atom, and $R_3$ represents a group represented by $\{(CH_2)_n S(CH_2)_m\}_L$ in which n, m and L each represent an integer of from 1 to 4; extracting palladium by the organic phase; and conducting a back-extraction of palladium, extracted by the organic phase, with an aqueous solution of hydrochloric acid containing thiourea.

8 Claims, 1 Drawing Sheet

U.S. PATENT DOCUMENTS

2002/0112569 A1* 8/2002 Farone et al. ................ 75/741
2003/0190274 A1* 10/2003 Singh ........................ 423/22

FOREIGN PATENT DOCUMENTS

| JP | 1-30896 | 6/1989 |
|---|---|---|
| JP | 3-22402 | 1/1991 |
| JP | 6-172882 | 6/1994 |
| JP | 7-310129 | 11/1995 |
| JP | 8-27527 | 1/1996 |
| JP | 8-158088 | 6/1996 |
| JP | 9-279264 | 10/1997 |
| JP | 10-102156 | 4/1998 |

OTHER PUBLICATIONS

Alizadeh, Naader; Liquid- liquid Extraction of Palladium from Hydrobromic Acid Meida by Hexadecylpyridium Bormide; Mar. 2002, The Japan Society for Analytical Chemistry, vol. 18.*

* cited by examiner

EXTRACTANT FOR PALLADIUM AND METHOD FOR SEPARATION AND RECOVERY OF PALLADIUM

TECHNICAL FIELD

The present invention relates to an extractant for palladium and a method for separation and recovery of palladium.

BACKGROUND ART

Platinum group metals such as platinum and palladium are employed in industrial catalysts, catalysts for purifying automotive exhaust gas, and various electrical products. Since such platinum group metals are expensive and useful as resources, they have been recovered and recycled after the use. Furthermore, recently, in consideration of securing the resources, importance of recovery and recycling has been further increasing.

For recovering the platinum group metals, various methods such as a sedimentation separation method (Patent document 1), an ion exchange method (Patent documents 2 and 3), an electrolytic precipitation method (Patent document 4), and a solvent extraction method have been proposed and exercised. Among these methods, the solvent extraction method is widely adopted for economical property and operability.

In the solvent extraction method, sulfur-containing organic compounds and organic phosphorous compounds have been employed. As the sulfur-containing organic compounds, dialkyl sulfide and dialkylsulfine oxide are utilized, and, as the organic phosphorous compound, trialkyl phosphonate, trialkyl phosphate, trialkylphosphine oxide and trialkylphosphine sulfide have been known, and there has been known a method of utilizing dialkyl sulfide (DAS) or tributylphosphoric acid (TBP) (Patent document 5). According to this method, palladium is extracted with DAS, and platinum is recovered by TBP. Since osmium and ruthenium are also extracted in DAS, there are required, in order to prevent such a contamination, operations of dissolving in aqua regia, oxidizing osmium and ruthenium into tetroxide, and subsequent heating for elimination by evaporation (Patent document 6).

However, this method involves problems such as requiring a large amount of oxidant. Because of this fact, it is considered effective to utilize DAS of a four times molar amount or larger with respect to the platinum group metals (Patent document 7). Among DAS, dihexyl sulfide (DHS) is generally utilized, but it is pointed out that there is a difficulty in the extracting speed.

Patent document 1: JP-A-10-102156
Patent document 2: JP-A-3-22402
Patent document 3: JP-A-7-310129
Patent document 4: JP-A-8-158088
Patent document 5: JP-A-63-14824
Patent document 6: JP-B-1-30896
Patent document 7: JP-A-9-279264

DISCLOSURE OF THE INVENTION

Problems to be Solved by the Invention

An object of the present invention is to provide a novel extractant for palladium capable of improving an extraction speed in comparison with a case of utilizing a DHS being a conventional extractant, and a method for separation and recovery of palladium utilizing the same.

Means for Solving the Problems

It is found by the present inventors that, by bringing a sulfur-containing diamide compound, as an extractant instead of DHS, into contact with a palladium-containing aqueous solution, while DHS being conventionally employed only shows a low extraction percentage initially and achieves a sufficient extraction percentage only after a while, the sulfur-containing diamide compound can achieve a sufficient extraction percentage from the start of the extraction process and can also extract palladium highly selectively from an acidic aqueous solution containing other platinum group metals and base metals, and the present invention has thus been made.

The present invention is as follows.

(1) An extractant for palladium comprising a sulfur-containing diamide compound represented by the following structural formula (1):

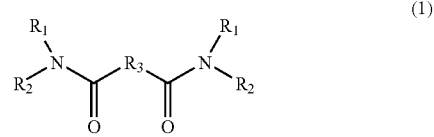

wherein $R_1$ and $R_2$ each represent a group selected from:
a chain hydrocarbon group having 1 to 18 carbon atoms which may be branched,
an alicyclic hydrocarbon group having 1 to 10 carbon atoms, and
an aromatic hydrocarbon group having 1 to 14 carbon atom; and
$R_3$ represents a group represented by $\{(CH_2)_nS(CH_2)_m\}_L$ wherein n, m and L each represent an integer of from 1 to 4.

(2) A method for separating palladium, which comprises bringing an aqueous solution containing palladium into contact with an organic phase containing the extractant for palladium according to (1) above in an acidic condition, thereby extracting palladium from the organic phase.

(3) A method for separating palladium, which comprises subjecting the palladium extracted by the organic phase according to (2) above to a back-extraction with an aqueous solution of hydrochloric acid containing thiourea, thereby obtaining an aqueous solution containing palladium.

(4) A method for separating and recovering platinum group metals including palladium, platinum and rhodium from a treated solution containing platinum group metals and base metals, which comprises:
neutralizing said treated solution containing platinum group metals including palladium, platinum and rhodium and base metals, thereby separating and eliminating, as a precipitate, metals other than the platinum group metals coexisting in said solution (first step);
bringing said solution containing platinum group metals including palladium, platinum and rhodium into contact with the extractant according to (1) above comprising a sulfur-containing diamide compound represented by the structural formula (1), thereby separating and recovering palladium from an acidic solution containing palladium (second step);
bringing said extractant for palladium containing palladium into contact with an aqueous solution of hydrochloric acid containing thiourea to recover palladium, thereby obtaining palladium (third step); and bringing said aqueous solution containing platinum and rhodium, which is obtainable in the second step, into contact with a tributylphosphoric acid-based extractant to extract and separate platinum from rhodium, thereby separating and recovering platinum and rhodium (fourth step).

EFFECT OF THE INVENTION

According to the present invention, it is possible, by employing a sulfur-containing diamide compound as an extractant for palladium among the platinum group metals, to extract palladium within a short time and to achieve a separation from other platinum group metals and base metals, thereby achieving separation and recovery of palladium with a high efficiency.

BEST MODE FOR CARRYING OUT THE INVENTION

Figure 1:
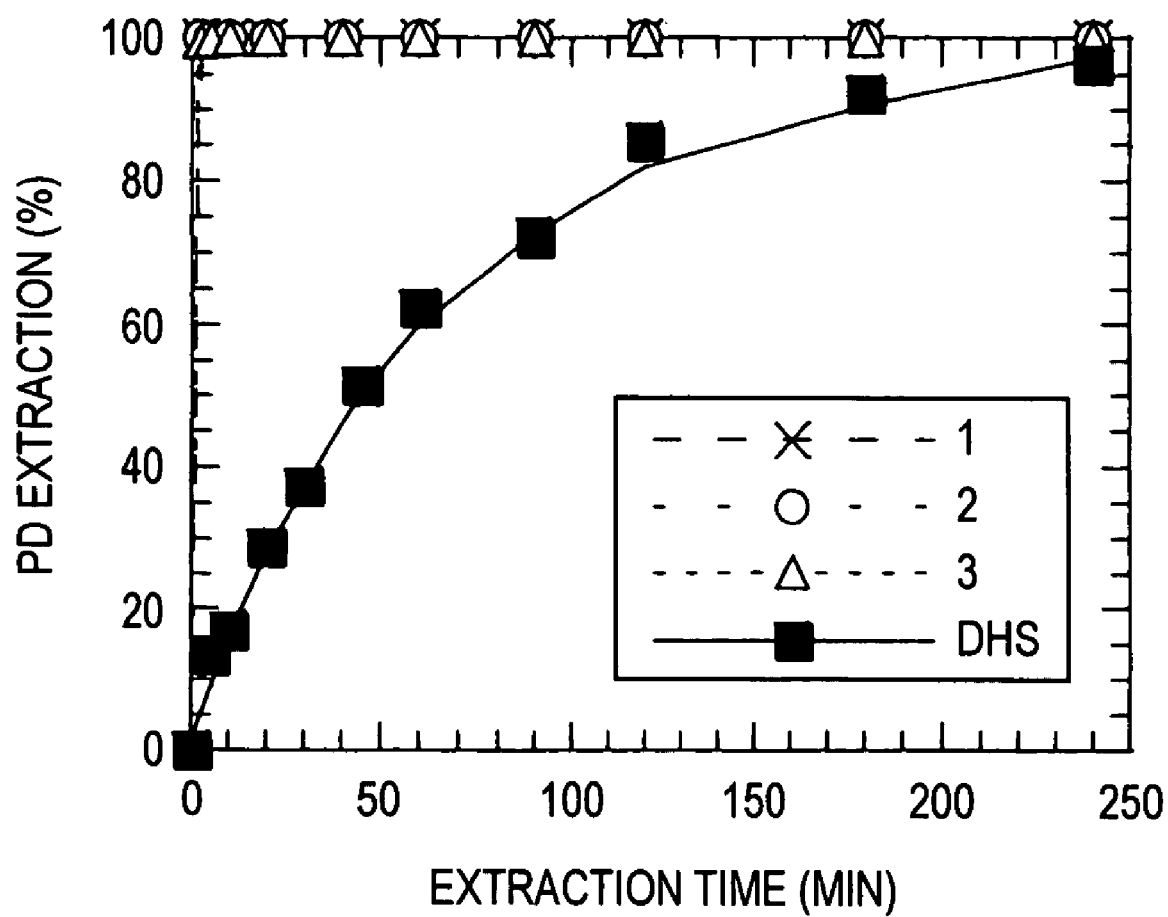
FIG. 1 is a drawing showing a dependence of palladium (II) extraction percentage on an extraction time.

An objective solution to be processed in the present invention can be obtained in the following manner.

An object to be processed, such as a used catalyst, is subjected to a reduction fusion to obtain an iron alloy containing platinum group metals. This alloy is subjected, after crushing, to a chlorine leaching step of leaching with chlorine, a reduced PGM recovery step of utilizing a metal as a reducing agent on the leached solution obtained by the chlorine leaching step to reduce the platinum group metals in the solution, thereby recovering the same as a platinum group metal concentrate, and a PGM dissolving step of dissolving the platinum group metal concentrate, obtained from the reduced PGM recovery step, with hydrochloric acid and an oxidant, to obtain a solution, which is used as the object solution.

The objective solution contains platinum group metals including palladium, platinum and rhodium. Components other than palladium are not essential.

The process steps above will be explained in further details.

The aforementioned chlorine leaching step is carried out at a pH of 1 or less, and carried out by mixing a solution having an iron chloride ion concentration of at least 15 g/l and powder of an iron alloy containing the platinum group metals, crushed to such a particle size that a portion having a diameter of 45 μm or less represents at least 45%, in a proportion of from 150 to 250 g, preferably from 200 to 250 g with respect to 1 L of the solution. In addition, it is preferably carried out by adding a small amount of nitric acid after the dissolution, followed by causing the solution to stand for 3 hours or longer.

The reduced PGM recovery step is carried out, utilizing, as a reducing agent, a metal or metal powder, preferably metal powder soluble in hydrochloric acid such as iron powder, with a solution pH of 0 or less at the reduction and with an oxidation-reduction potential of from −100 to +100 mV, preferably from −60 to +100 mV, with respect to a silver-silver chloride electrode.

The aforementioned redissolving step is to be carried out with a reaction temperature of 90° C. or higher and a slurry concentration of from 200 to 400 g/l, so as to obtain a copper ion concentration of from 20 to 30 g/l and a chlorine ion concentration of 9 mol/l or higher in the solution at the end of dissolution, and the oxidant to be employed in this step is chlorine, hydrogen peroxide, oxygen or air, preferably chlorine.

In the present invention, the thus obtained objective solution to be processed is at first subjected to a following process (first step).

The hydrochloric acid solution of platinum group metals, which is obtained in the redissolving step, is neutralized in order to separate and eliminate the metals other than the platinum group metals, which coexist in the solution as precipitates. This impurity eliminating step by neutralization is carried out at a pH of from 2.8 to 3.3, and more preferably by adjusting the pH after eliminating an excessive oxidant, for example, by a degassing.

The solution obtained by the operations above contains platinum group metals such as palladium, platinum and rhodium. Among these platinum group metals, components other than palladium, namely platinum and rhodium, are contained depending on the object to be processed.

There is prepared a hydrochloric acid solution containing palladium, at a metal molar concentration equal to ½ of the molar concentration of the sulfur-containing diamide compound, to be contacted with the solution to be processed.

The sulfur-containing diamide compound is presented by the following structural formula:

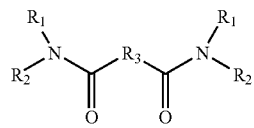

(In the formula, $R_1$ and $R_2$ each represent a group selected from a chain hydrocarbon group having 1 to 18 carbon atoms which may be branched, an alicyclic hydrocarbon group having 1 to 10 carbon atoms, and an aromatic hydrocarbon group having 1 to 14 carbon atom; and $R_3$ represents a group represented by $\{(CH_2)_nS(CH_2)_m\}_L$ in which n, m and L each represent an integer of from 1 to 4.).

Examples of the chain hydrocarbon group include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, isopropyl, isobutyl, s-butyl, t-butyl, isopentyl, neopentyl, t-pentyl, 2-ethylhexyl, vinyl, allyl, 1-propenyl, isopropenyl, 1-butenyl, 2-butenyl, 2-methylallyl, 1-heptinyl, 1-hexenyl, 1-heptenyl, 1-octenyl, and 2-methyl-1-propenyl. Examples of the alicyclic hydrocarbon group include cyclobutyl, cyclopentyl, cyclohexyl, cycloheptyl, cyclooctyl, cyclononyl, cyclodecyl, cyclohexenyl, cyclohexadienyl, cyclohexatrienyl, cyclooctenyl, and cyclooctadienyl. Examples of the aromatic hydrocarbon group include phenyl, naphthyl, anthryl, tolyl, xylyl, cumenyl, benzyl, phenethyl, styryl, cinnamyl, biphenylyl and phenanthryl.

These substances may be obtained by reacting an acid chloride such as thiodiglycolyl chloride and a secondary amine such as dialkylamine. These substances may be available from commercial products.

Compounds included in those mentioned above are shown in the followings.

A thiodiglycolamide compound is as follows:

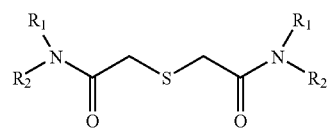

(In the formula, $R_1$ and $R_2$ each represent a group selected from a chain hydrocarbon group having 1 to 18 carbon atoms which may be branched, an alicyclic hydrocarbon group having 1 to 10 carbon atoms, and an aromatic hydrocarbon group having 1 to 14 carbon atom.).

A 3,3'-thiopropionamide compound is as follows:

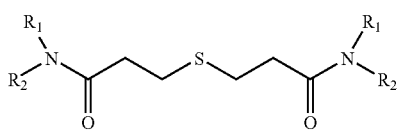

(In the formula, $R_1$ and $R_2$ each represent a group selected from a chain hydrocarbon group having 1 to 18 carbon atoms which may be branched, an alicyclic hydrocarbon group having 1 to 10 carbon atoms, and an aromatic hydrocarbon group having 1 to 14 carbon atom.).

A 3,6-dithiaoctandediamide compound is as follows:

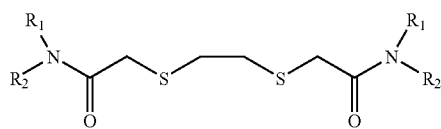

(In the formula, $R_1$ and $R_2$ each represent a group selected from a chain hydrocarbon group having 1 to 18 carbon atoms which may be branched, an alicyclic hydrocarbon group having 1 to 10 carbon atoms, and an aromatic hydrocarbon group having 1 to 14 carbon atom.).

In the method of the present invention, an extracting solution containing an extracting solvent is prepared.

The substance may be used by dissolving in a hydrophobic organic solvent, for example, an aliphatic hydrocarbon such as n-dodecane, an alcohol such as 2-ethyl-1-hexanol, an aliphatic chloride such as chloroform, or an aromatic hydrocarbon such as benzene. A concentration of the extractant in the solvent may be suitably determined, but a separation of palladium may be lowered under a high concentration of the extractant.

An aqueous phase which is constituted of the aqueous solution of hydrochloric acid containing the platinum group metals and an organic phase containing the sulfur-containing diamide compound are contacted (second step).

Palladium is almost entirely extracted in the organic phase immediately after the contact, but other platinum group metals such as platinum and rhodium are scarcely extracted but remain in the aqueous phase.

Base metals such as copper, iron and zinc are removed in advance from the aqueous phase in the second step, but, even when such base metals remain, palladium alone is almost entirely extracted in the organic phase.

Palladium, separated in the organic phase by the aforementioned operation, can be recovered, by a contact with an aqueous solution of hydrochloric acid containing thiourea, as an aqueous solution (third step).

A solution of platinum and rhodium, obtained from the step of eliminating trace impurity remaining in water in the aforementioned operation, is contacted with TBP to extract and separate platinum from rhodium (fourth step). For achieving an efficient extraction of platinum, it is necessary to regulate the total chlorine ion concentration in the aqueous solution at 4 to 5 mol/l.

The TBP-containing organic solvent after platinum extraction is heated to a temperature equal to or higher than 90° C. but not exceeding the boiling temperature, then an oxidant and an alkali are added, and a hydroxide is filtered off to obtain a purified platinum solution, to which ammonium chloride is added to recover platinum as platinum ammonium chloride.

The rinsing after the extraction is preferably carried out, in order to prevent a back-extraction of platinum as far as possible and to retain rhodium chloro-complex, by employing an as little amount as possible of hydrochloric acid solution of 4 mol/l or higher, preferably 6 mol/l, and the rinsing may be made twice or more at O/W=1/28 to 1/30 (v/v).

As a result of these operations, a purified platinum solution having a low rhodium content is recovered as a back-extracted solution, and an effective yield for platinum of 99% or higher is made possible. On the other hand, a loss in rhodium is 0.1% or less, so that an effective separation is realized.

Through the operations above, metals other than rhodium only remain in very small amounts in the aqueous solution, and rhodium is precipitated as rhodium hydroxide, by adjusting pH at 9 or higher with an alkali and heating to a temperature of 90° C. or higher. After the solid-liquid separation, it is preferable, in order to remove the adhering water, to wash the precipitate with warm water of pH 12 or higher, and then to conduct a repulping washing with warm water. As a result, purified rhodium hydroxide can be recovered.

In the following, examples will be shown for further clarifying the features of the present invention, but the present invention is not restricted by the examples.

EXAMPLE 1

Cases of Comparative Example (di-n-hexyl sulfide (DHS), Example 1 (N,N'-dimethyl-N,N'-diphenyl-thiodiglycolamide (1)), Example 2 (N,N'-dimethyl-N,N'-diphenyl-3,3'-thiodipropionamide (2)), and Example 3 N,N'-dimethyl-N,N'-diphenyl-3,6-dithiaoctanediamide (3)).

Each of a prior separation reagent di-n-hexyl sulfide (DHS), N,N'-dimethyl-N,N'-diphenyl-thiodiglycolamide (1), N,N'-dimethyl-N,N'-diphenyl-3,3'-thiodipropionamide (2), and N,N'-dimethyl-N,N'-diphenyl-3,6-dithiaoctanediamide (3) was diluted with chloroform to 0.1 mol/l. Each of these organic solvent was added with an equal amount of a 3 mol/l hydrochloric acid solution containing palladium at 50 mg/l and shaken vigorously to extract palladium in the organic phase. The extraction percentage was determined by measuring the metal concentration in the aqueous phase before and after the shaking, by an ICP atomic emission spectrometer. A change in the extraction percentage at different shaking times is shown in FIG. 1.

It can be seen that, while DHS requires about 240 minutes for extracting an almost entire amount of palladium, 1, 2 and 3 can extract an almost entire amount immediately after the contact of the organic phase and the aqueous phase. Based on this, it can be concluded that 1, 2 and 3 are faster in the palladium extraction.

EXAMPLE 2

Processing of a hydrochloric acid solution in which palladium, platinum, rhodium, and base metals including copper, iron and zinc are coexistent.

An extraction percentage of metals into an organic phase containing 1, 2 or 3, from a hydrochloric acid solution in which palladium, platinum, rhodium, and base metals including copper, iron and zinc are coexistent, was determined (Table 1).

An aqueous solution of hydrochloric acid having a concentration of 0.4 or 3 mol/l and containing metals each at 50 mg/l was employed as the aqueous phase. The organic phase for extraction was prepared by diluting an extractant to 0.1 mol/l with chloroform. Metals were extracted by shaking the organic phase and the aqueous phase for 10 minutes vigorously. The extraction percentage was determined by measuring the metal concentration in the aqueous phase before and after the shaking, with an ICP atomic emission spectrometer. It was found that palladium was about 100% extracted in the organic phase. On the other hand, it was found that other platinum group metals and the base metals were scarcely extracted in the organic phase.

TABLE 1

| | Extractant | | | | | |
|---|---|---|---|---|---|---|
| | 1 | | 2 | | 3 | |
| | hydrochloric acid concentration at extraction (mol/l) | | | | | |
| | 0.4 | 3.0 | 0.4 | 3.0 | 0.4 | 3.0 |
| Pd (II) | 99.9% | 100% | 99.9% | 100% | 99.9% | 99.7% |
| Pt (IV) | 0.0% | 0.9% | 0.0% | 0.1% | 5.1% | 0.8% |
| Rh (III) | 4.1% | 4.8% | 1.8% | 3.9% | 0.0% | 5.3% |
| Cu (II) | 2.7% | 4.5% | 2.1% | 4.7% | 0.0% | 5.1% |
| Fe (III) | 2.9% | 2.7% | 0.0% | 0.9% | 4.0% | 2.5% |
| Zn (II) | 0.0% | 4.1% | 2.0% | 3.0% | 0.0% | 4.3% |

Based on these results, it can be concluded that, by bringing an aqueous solution of hydrochloric acid into contact with 1, 2 or 3 diluted with chloroform to 0.1 mol/l, palladium can be almost entirely extracted and selectively separated.

Also the organic phase, in which palladium is extracted, is separated, and a 1 mol/l thiourea solution formed by dissolving in a 1 mol/l hydrochloric solution of a same amount is added as the aqueous phase, and shaken for 10 minutes to execute a back-extraction of palladium into the aqueous phase. A back-extraction percentage and a recovery percentage (extraction percentage×back-extraction percentage/100) in this operation are shown in Table 2. It is indicated that, in experiments of back-extraction on the organic phase, with the aqueous phase having a hydrochloric acid concentration of 0.4 or 3 mol/l at palladium extraction, palladium is back-extracted by 90% or more in both cases. These results are obtained by a single operation, and a value close to 100% can be obtained by repeating this operation several times.

TABLE 2

| | Extractant | | | | | |
|---|---|---|---|---|---|---|
| | 1 | | 2 | | 3 | |
| | hydrochloric acid concentration in aqueous phase at palladium extraction (mol/l) | | | | | |
| | 0.4 | 3.0 | 0.4 | 3.0 | 0.4 | 3.0 |
| Pd back-extraction (%) | 94.8 | 95.4 | 90.8 | 94.6 | 92.9 | 95.8 |
| Pt recovery (%) | 94.7 | 95.4 | 90.7 | 94.6 | 92.8 | 95.5 |

Based on the foregoing results, it can be concluded that palladium can be completely separated from a hydrochloric acid solution of metal ions in which palladium, platinum, rhodium, and copper, ion and zinc as base metals are coexistent, by a contact with an organic phase containing 1, 2 or 3, and that palladium taken into the organic phase can be completely recovered by a contact with an aqueous solution of thiourea having a specified hydrochloric acid concentration. It is therefore concluded that 1, 2 or 3 as an extractant can separate and recover palladium within a short time in comparison with the conventional methods.

The invention claimed is:

1. An extractant for palladium comprising a sulfur-containing diamide compound represented by the following structural formula (1):

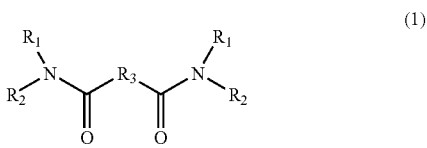

wherein $R_1$ and $R_2$ each represent a group selected from:
a chain hydrocarbon group having 1 to 18 carbon atoms which may be branched,
an alicyclic hydrocarbon group having 1 to 10 carbon atoms, and
an aromatic hydrocarbon group having 1 to 14 carbon atoms, and
$R_3$ represents a group represented by $\{(CH_2)_nS(CH_2)_m\}_L$ wherein n, m and L each represent an integer of from 1 to 4.

2. A method for separating palladium, which comprises bringing an aqueous solution containing palladium into contact with an organic phase containing the extractant for palladium according to claim 1 in an acidic condition, thereby extracting palladium from the organic phase.

3. A method for separating palladium, which comprises subjecting the palladium extracted by the organic phase according to claim 2 to a back-extraction with an aqueous solution of hydrochloric acid containing thiourea, thereby obtaining an aqueous solution containing palladium.

4. A method for separating and recovering platinum group metals including palladium, platinum and rhodium from a treated solution containing platinum group metals and base metals, which comprises:

(a) neutralizing said treated solution containing platinum group metals including palladium, platinum and rhodium and base metals, thereby separating and eliminating, as a precipitate, metals other than the platinum group metals coexisting in said solution (first step); bringing said solution containing platinum group metals including palladium, platinum and rhodium into contact with the extractant according to claim 1 comprising a sulfur-containing diamide compound represented by the structural formula (1), thereby separating and recovering palladium from an acidic solution containing palladium (second step);

(b) bringing said extractant for palladium containing palladium into contact with an aqueous solution of hydrochloric acid containing thiourea to recover palladium, thereby obtaining palladium (third step); and (c) bringing said aqueous solution containing platinum and rhodium, which is obtainable in the second step, into contact with a tributylphosphoric acid-based extractant to extract and separate platinum from rhodium, thereby separating and recovering platinum and rhodium (fourth step).

5. An extractant for palladium comprising a sulfur-containing diamide compound of claim 1, wherein the aromatic hydrocarbon group having 1-14 carbon atom is selected from the group consisting of phenyl, naphthyl, anthryl, xylyl, cumenyl, benzyl, phenylethyl, styryl, cinnamyl, biphenylyl, and phenathryl.

6. An extractant for palladium comprising a sulfur-containing diamide compound of claim 1, wherein the alicyclic hydrocarbons having 1 to 10 carbon atoms is selected from the group consisting of cyclobutyl, cyclopentyl, cyclohexyl, cycloheptyl, cyclooctyl, cyclononyl, cyclodecyl, cyclohexenyl, cyclohexadienyl, cyclohexatrienyl, cyclooctenyl, and cyclooctadienyl.

7. An extractant for palladium comprising a sulfur-containing diamide compound of claim 1, wherein the chain hydrocarbon group having 1 to 18 carbon atoms is selected from the group consisting of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, isopropyl, isobutyl, s-butyl, t-butyl, isopentyl, neopentyl, t-pentyl, 2-ethylhexyl, vinyl, allyl, 1-propenyl, isopropenyl, 1-butenyl, 2-butenyl, 2-methylallyl, 1-heptinyl, 1-hexenyl, 1-heptenyl, 1-octenyl, and 2-methyl-1-propenyl.

8. An extractant for palladium comprising a sulfur-containing diamide compound of claim 1, wherein $R_3$ represents a group represented by $\{(CH_2)_n S(CH_2)_m\}_L$ wherein n, m each represent an integer of from 1 to 4 and wherein L is 1.

* * * * *